US011754753B2

(12) United States Patent
Maltseva et al.

(10) Patent No.: US 11,754,753 B2
(45) Date of Patent: Sep. 12, 2023

(54) ANTIOXIDANT CONTACT LENS

(71) Applicant: CooperVision International Limited, Fareham (GB)

(72) Inventors: Inna Maltseva, San Francisco, CA (US); Nancy J. Keir, Pleasanton, CA (US); Andrew Luk, Pleasanton, CA (US); Victoria Rogers, Pleasanton, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 317 days.

(21) Appl. No.: 17/228,748

(22) Filed: Apr. 13, 2021

(65) Prior Publication Data

US 2021/0333436 A1    Oct. 28, 2021

Related U.S. Application Data

(60) Provisional application No. 63/015,765, filed on Apr. 27, 2020.

(51) Int. Cl.
| | |
|---|---|
| G02B 1/04 | (2006.01) |
| A45C 11/00 | (2006.01) |
| A61K 9/00 | (2006.01) |
| A61K 31/355 | (2006.01) |
| C08J 3/075 | (2006.01) |
| C08K 5/1545 | (2006.01) |

(52) U.S. Cl.
CPC ............ *G02B 1/043* (2013.01); *A45C 11/005* (2013.01); *A61K 9/0051* (2013.01); *A61K 31/355* (2013.01); *C08J 3/075* (2013.01); *C08K 5/1545* (2013.01); *C08J 2333/26* (2013.01); *C08J 2383/04* (2013.01)

(58) Field of Classification Search
None
See application file for complete search history.

(56) References Cited

U.S. PATENT DOCUMENTS

| | | | |
|---|---|---|---|
| 3,977,517 A | 8/1976 | Kadlecik et al. | |
| 6,867,245 B2 | 3/2005 | Iwata et al. | |
| 7,319,133 B2 | 1/2008 | Brame et al. | |
| 7,426,993 B2 | 9/2008 | Coldrey et al. | |
| 8,231,218 B2 | 7/2012 | Hong et al. | |
| 8,404,265 B2 | 3/2013 | Chauhan et al. | |
| 8,623,400 B2* | 1/2014 | Liu ...................... | A61K 9/0051 424/429 |
| 8,658,747 B2 | 2/2014 | Liu et al. | |
| 8,784,867 B2 | 7/2014 | Samuel et al. | |
| 8,865,789 B2 | 10/2014 | Yao et al. | |
| 8,937,133 B2* | 1/2015 | Liu ...................... | C08F 220/20 525/342 |
| 9,216,106 B2 | 12/2015 | Schultz et al. | |
| 2002/0164379 A1* | 11/2002 | Nishihara .............. | A61K 33/00 424/600 |
| 2012/0218509 A1* | 8/2012 | Back ...................... | C08L 83/04 351/159.33 |
| 2013/0178518 A1* | 7/2013 | Samuel .................. | G02B 1/043 514/458 |
| 2014/0288206 A1* | 9/2014 | Chauhan ................ | G02B 1/043 264/494 |
| 2016/0062142 A1* | 3/2016 | Zhang ............... | B29D 11/00865 427/164 |
| 2016/0086517 A1* | 3/2016 | Gao ........................ | G09B 23/34 434/271 |
| 2017/0166673 A1* | 6/2017 | Huang ................. | C08G 77/392 |
| 2019/0015521 A1 | 1/2019 | Roizman | |
| 2021/0333436 A1* | 10/2021 | Maltseva .............. | A45C 11/005 |

FOREIGN PATENT DOCUMENTS

| | | |
|---|---|---|
| CN | 1383383 A | 12/2002 |
| CN | 107260655 A | 10/2017 |
| CN | 108853116 A | 11/2018 |
| JP | 2015-28090 A | 2/2015 |
| JP | 2017165778 A | 9/2017 |
| JP | 2020034945 A | 3/2020 |
| TW | I509313 B | 11/2015 |
| TW | 201902468 A | 1/2019 |
| WO | 2019224662 A1 | 11/2019 |

OTHER PUBLICATIONS

Extended release of dexamethasone from silicone-hydrogel contact lenses containing vitamin E, Journal of Controlled Release, 148, (2010) 110-116 (Year: 2010).*
Office Action issued in corresponding Japanese Patent Application No. 2022-565795 dated Mar. 6, 2023 (with English translation)(8 pages).
Search Report issued in corresponding United Kingdom Patent Application No. GB2105896.1 dated Oct. 6, 2021 (4 pages).
Dixon et al., "Spectroscopy of Oxygen-Sensitive Material for Measuring Contact Lens Oxygen Transmissibility," Current Eye Research, 2019, vol. 44, No. 5, pp. 514-521.
International Search Report and Written Opinion issued in corresponding International Patent Application No. PCT/GB2021/051002 dated Jul. 23, 2021 (16 pages).
PCT Demand filed Jan. 26, 2022 in corresponding International Patent Application No. PCT/GB2021/051002 (24 pages).

(Continued)

*Primary Examiner* — Peter A Salamon
(74) *Attorney, Agent, or Firm* — Kilyk & Bowersox, P.L.L.C.

(57) ABSTRACT

A contact lens having antioxidant properties is described as well as methods of manufacturing the same. The contact lens can be present in a sealed contact lens package. The seal contact lens package can include at least a) a plastic base member having a cavity; b) a contact lens packaging solution in the cavity; c) a sterile, unworn contact lens immersed in the contact lens packaging solution in the cavity; and d) a cover that forms a liquid-tight seal with the plastic base member. As an example, the unworn contact lens is a silicone hydrogel contact lens having present therein vitamin E. The vitamin E is non-releasable from the unworn contact lens and the contact lens packaging solution has less than 1 ppm of vitamin E present. The vitamin E is trapped, embedded, absorbed, or non-covalently attached in the unworn contact lens.

10 Claims, No Drawings

(56) References Cited

OTHER PUBLICATIONS

Second Written Opinion issued in corresponding International Patent Application No. PCT/GB2021/051002 dated Feb. 16, 2022 (9 pages).
International Preliminary Report on Patentability issued in corresponding International Patent Application No. PCT/GB2021/051002 dated Aug. 24, 2022 (with copy of response to Second Written Opinion filed Apr. 13, 2022 and Article 34 claims) (23 pages).
Office Action issued in corresponding Taiwan Patent Application No. 110115051 dated Sep. 6, 2022 (with English translation)(17 pages).
Wakamatsu et al., "Tearful relations: oxidative stress, inflammation and eye diseases," Arq Bras Oftalmol, 2008, vol. 71, 6 Supl, pp. 72-79.
Choi et al., "Are Sensory TRP Channels Biological Alarms for Lipid Peroxidation?," Int. J. Mol. Sci., 2014, vol. 15, pp. 16430-16457.

\* cited by examiner

ANTIOXIDANT CONTACT LENS

This application claims the benefit under 35 U.S.C. § 119(e) of prior U.S. Provisional Patent Application No. 63/015,765, filed Apr. 27, 2020, which is incorporated in its entirety by reference herein.

FIELD

The field of the invention relates to contact lenses, and particularly, contact lenses having antioxidant properties, and further relates to packages containing the contact lenses, and methods of manufacturing the contact lenses. The contact lenses of the present invention having the antioxidant properties can be considered antioxidant contact lenses.

BACKGROUND

Tear fluid holds various antioxidant molecules such as enzymes and vitamins, which protect the eye and ocular surface from the effects of light, UV radiation, and chemical agents that could initiate oxidation. The function of antioxidants is to capture and react with free radicals at a rate faster than the substrate. Oxidative stress is caused by an imbalance between the production of reactive oxygen species and ability of the biological systems' defense mechanisms to eliminate the stress. Since free radicals can interact with a variety of targets including lipids, fats, and proteins, they have been implicated in the pathogenesis of a number of degenerative disorders including ocular surface diseases such as dry eye (1). A potential mechanism might include changes to the tear lipid layer and reduced ability to protect the aqueous layer from evaporation. Lipid oxidation and peroxidation (LPO) products also appear to be important steps in various types of inflammation and have also been shown to activate sensory pain receptors, i.e. TRPV1 and TRPA1 (2).

Contact lenses bind various lipids secreted by the Meibomian glands and derived from cell membranes, which are subject to lipid peroxidation and production of LPO products. A contact lens with antioxidant properties may protect such lipids from peroxidation, in turn reducing LPO products and potentially minimizing pain receptor activation, leading to an enhancement in the comfort of the contact lens. Thus, there is a need in the industry for contact lenses that provide such antioxidant properties. However, it would also be desirable to provide such antioxidant properties without significantly affecting other properties that are provided by contact lenses, especially silicone hydrogel lenses.

BACKGROUND REFERENCES

1. Wakamatsu T H, Dogru M, Tsubota K. Tearful relations: oxidative stress, inflammation and eye diseases. Arg Bras Oftalmol 2008.
2. Seung-In Choi et al., Are Sensory TRP Channels Biological Alarms for Lipid Peroxidation? Int. J. Mol. Sci. 2014

SUMMARY

A feature of the present invention is to provide a silicone hydrogel contact lens having antioxidant properties.

An additional feature of the present invention is to provide an unworn, sterile contact lens that is a silicone hydrogel and having antioxidant properties when worn or placed on the eye.

A further feature of the present invention is to provide a silicone hydrogel contact lens that does not release any bioactive agent nor any agent added that provides antioxidant properties.

An additional feature of the present invention is to provide a silicone hydrogel contact lens having vitamin E present therein that provides antioxidant properties and that is fully hydrated, but without significantly decreasing the amount of aqueous liquid needed to fully hydrate, as compared to the same type of silicone hydrogel contact lens without vitamin E present.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention, in part, relates to a sealed contact lens package. The sealed contact lens package includes at least a) a plastic base member having a cavity; b) a contact lens packaging solution in the cavity; c) a sterile, unworn contact lens immersed in the contact lens packaging solution in the cavity; and d) a cover that forms a liquid-tight seal with the plastic base member. Further, the unworn contact lens is a silicone hydrogel contact lens having present therein at least 10 μg or at least 20 μg of vitamin E per 25 mg of the sterile, unworn contact lens when fully hydrated and having 0 μg of a bioactive agent (wherein the vitamin E, for purposes of the present invention, is not considered a bioactive agent). The vitamin E is non-releasable from the unworn contact lens. The contact lens packaging solution has less than 1 ppm of vitamin E present.

The present invention further relates to an unworn antioxidant contact lens immersed in a packaging solution and sterilely sealed in a package. The contact lens comprises a silicone hydrogel and an amount of vitamin E embedded within the silicone hydrogel effective to provide at least a 50% reduction in lipid peroxidation relative to a control contact lens lacking the vitamin E when measured in a TBARS assay. Further, the antioxidant contact lens is free of a bioactive agent having a release profile attenuated by the vitamin E.

In addition, the present invention relates to an unworn antioxidant contact lens immersed in a packaging solution and sterilely sealed in a package. The contact lens comprises a silicone hydrogel and an amount of vitamin E embedded within the silicone hydrogel effective to provide at least a 50% reduction in lipid peroxidation relative to a control contact lens lacking the vitamin E when measured in a TBARS assay. And, the antioxidant contact lens has (a) an ophthalmically-acceptable surface wettability in the absence of a post curing surface treatment and (b) an advancing contact angle that is no more than 10° greater than the control lens.

Furthermore, the present invention relates to an unworn antioxidant contact lens immersed in a packaging solution and sterilely sealed in a package. The contact lens comprises a silicone hydrogel and 10 μg to 1000 μg of vitamin E embedded in the silicone hydrogel. Also, the antioxidant contact lens (a) has a heat stability that is no greater than a control contact lens lacking the vitamin E and (b) is free of a bioactive agent having a release profile attenuated by the vitamin E.

The present invention further relates to a method to control lipid peroxidation from tear film in an eye of a person wearing a contact lens. The method can include the step of inserting a sterile, unworn contact lens in the eye of the person to correct vision in the eye of the person. The sterile, unworn contact lens is a silicone hydrogel contact lens having therein an amount of vitamin E. For instance, at least 10 μg or at least 20 μg of vitamin E per 25 mg of the sterile, unworn contact lens when fully hydrated can be present and 0 μg of a bioactive agent. The other amounts for vitamin E mentioned herein can be used instead. In the method, the vitamin E is non-releasable from the sterile, unworn contact lens when worn in the eye.

It is to be understood that both the foregoing general description and the following detailed description are exemplary and explanatory only and are intended to provide a further explanation of the present invention, as claimed.

DETAILED DESCRIPTION

Contact lenses having antioxidant properties and their method of manufacture are described herein. The contact lens or lenses having the antioxidant property or properties is at time referred to, herein, as an antioxidant contact lens.

In the present invention, the antioxidant contact lens preferably reduces peroxidation of lipids from the tear film that come in contact with the contact lens, which can improve contact lens comfort in at least some wearers.

In the present invention, the contact lens having the antioxidant properties is a silicone hydrogel contact lens having vitamin E present within the silicone hydrogel. The vitamin E can be uniformly distributed throughout the silicone hydrogel. As an option, the vitamin E can be non-uniformly distributed. For instance, the vitamin E can be present in higher amount on a side of the contact lens or on both sides of the contact lens (i.e., the posterior and anterior sides).

With respect to the vitamin E component, the vitamin E may include any combination of the tocopherols and tocotrienols of vitamin E and/or salts thereof and/or derivatives thereof. The tocopherols of vitamin E are α-tocopherol, β-tocopherol, γ-tocopherol, and δ-tocopherol. The tocotrienols of vitamin E are α-tocotrienol, β-tocotrienol, γ-tocotrienol, and δ-tocotrienol. The vitamin E may be synthetic or naturally occurring. Naturally occurring α-tocopherol is sometimes referred to as RRR-α-tocopherol or d-α tocopherol. Synthetic α-tocopherol is sometimes referred to as all-rac-α-tocopherol or dl-α-tocopherol. Commercially available derivatives of vitamin E include α-tocopherol acetate, α-tocopherol succinate and α-tocopherol nicotinate. In one example the vitamin E comprises at least 50 wt %, 60 wt %, 70 wt %, 80 wt %, 90 wt %, 95 wt % or 99 wt % α-tocopherol.

References herein to "an example" or "a specific example" or "an aspect" or "an embodiment" or similar phrase, are intended to introduce a feature or features of the antioxidant contact lens, or components thereof, or method of manufacturing the antioxidant contact lens (depending on context) that can be combined with any combination of previously-described or subsequently-described examples, aspects, embodiments (i.e. features), unless a particular combination of features is mutually exclusive, or if context indicates otherwise. Further, as used in this specification, the singular forms "a," "an," and "the" include plural referents (e.g. at least one or more) unless the context clearly dictates otherwise. Thus, for example, reference to a "contact lens" includes a single lens as well as two or more of the same or different lenses.

The vitamin E present within the silicone hydrogel or within the silicone hydrogel contact lens is not covalently attached. The vitamin E is embedded, trapped, dispersed, absorbed, and/or located within the contact lens. As used herein, the phrase "embedded within the silicone hydrogel" or "present within the silicone hydrogel" is intended to mean that the vitamin E is physically trapped within, and retained by, the silicone hydrogel polymer matrix such as by hydrophobic interactions as opposed to being chemically bound to it such as by covalent attachment.

The vitamin E may be trapped within a silicone hydrogel contact lens during the solvent extraction step after the contact lens material is cured, as described below.

The vitamin E is non-releasable meaning that the vitamin E, itself, is not released from the contact lens during autoclave, or storage in its packaging solution, or during lens wear. Thus, the packaging solution that the contact lens is immersed in, before autoclaving, or immediately after autoclaving, or after 1 day thereafter, or after 30 days thereafter, or after 60 days thereafter, or after 120 days thereafter has less than 1 ppm vitamin E present in the packaging solution or less than 0.1 ppm vitamin E, or 0 ppm vitamin E present in the packaging solution. Whether vitamin E is released from a contact lens during autoclave or storage can be determined by testing for the presence of vitamin E in the packaging solution using the HPLC method described in Example 1 below. Whether vitamin E is capable of releasing from a contact lens during wear can be predicted by placing the lens in a container with 3 mL of 5 vol % ethanol in water for 3 hours at 35° C. and mixing at 125 rpm. The ethanol solution is then tested by HPLC for the presence of vitamin E using the method described in Example 1. If less than 1 ppm vitamin E is detected, the vitamin E within the contact lens is considered non-releasable.

The antioxidant contact lens is preferably made from or is a silicone hydrogel material.

A silicone hydrogel material is typically formed by curing a polymerizable composition (i.e. a monomer mixture) comprising at least one siloxane monomer and at least one hydrophilic monomer or at least one hydrophilic polymer, or a combination thereof. As used herein, the term "siloxane monomer" is a molecule that contains at least one Si—O group and at least one polymerizable group. Siloxane monomers useful in contact lens compositions are well-known in the art (see, e.g., U.S. Pat. Nos. 8,658,747 and 6,867,245). (All patents and publications mentioned here and throughout are incorporated in their entirety by reference.) In some examples, the polymerizable composition comprises a total amount of siloxane monomer of at least 10 wt. %, 20 wt. %, or 30 wt. % up to about 40 wt. %, 50 wt. %, 60 wt. %, or 70 wt. %. Unless specified otherwise, as used herein, a given weight percentage (wt. %) of a component of the polymerizable composition is relative to the total weight of all polymerizable ingredients and IPN polymers (as described further below) in the polymerizable composition. The weight of the polymerizable composition contributed by components, such as diluents, that do not incorporate into the final contact lens product are not included in the wt. % calculation.

In a specific example, the polymerizable composition comprises a hydrophilic vinyl monomer. As used-herein, a "hydrophilic vinyl monomer" is any siloxane-free (i.e. contains no Si—O groups) hydrophilic monomer having a polymerizable carbon-carbon double bond (i.e., a vinyl group) present in its molecular structure that is not part of an acryl group, where the carbon-carbon double bond of the vinyl group is less reactive than the carbon-carbon double bond present in a polymerizable methacrylate group under free radical polymerization. As used herein, the term "acryl group" refers to the polymerizable group present in acrylate, methacrylates, acrylamides, etc. Thus, while carbon-carbon double bonds are present in acrylate and methacrylate groups, as used herein, such polymerizable groups are not considered to be vinyl groups. Further, as used herein, a monomer is "hydrophilic" if at least 50 grams of the monomer are fully soluble in 1 liter of water at 20° C. (i.e., ~5% soluble in water) as determined visibly using a standard shake flask method. In various examples, the hydrophilic vinyl monomer is N-vinyl-N-methylacetamide (VMA), or N-vinyl pyrrolidone (NVP), or 1,4-butanediol vinyl ether (BVE), or ethylene glycol vinyl ether (EGVE), or diethylene glycol vinyl ether (DEGVE), or any combination thereof. In one example, the polymerizable composition comprises at least 10 wt. %, 15 wt. %, 20 wt. %, or 25 wt. % up to about 45 wt. %, 60 wt. %, or 75 wt. % of a hydrophilic vinyl monomer. As used herein, a given weight percentage of a particular class of component (e.g., hydrophilic vinyl monomer, siloxane monomer, or the like) in the polymerizable composition equals the sum of the wt. % of each ingredient in the composition that falls within the class. Thus, for example, a polymerizable composition that comprises 5 wt. % BVE and 25 wt. % NVP and no other hydrophilic vinyl monomer, is said to comprise 30 wt. % hydrophilic vinyl monomer. In one example, the hydrophilic vinyl monomer is a vinyl amide monomer. Exemplary hydrophilic vinyl amide monomers are VMA and NVP. In a specific example, the polymerizable composition comprises at least 25 wt. % of a vinyl amide monomer. In a further specific example, the polymerizable composition comprises from about 25 wt. % up to about 75 wt. % of VMA or NVP, or a combination thereof. Additional hydrophilic monomers that may be included in the polymerizable composition are N,N-dimethylacrylamide (DMA), 2-hydroxyethyl methacrylate (HEMA), ethoxyethyl methacrylamide (EOEMA), ethylene glycol methyl ether methacrylate (EGMA), and combinations thereof.

In addition, or as an alternative to a hydrophilic monomer, the polymerizable composition may comprise a non-polymerizable hydrophilic polymer, which results in a polymeric lens body comprising an interpenetrating polymer network (IPN) with the non-polymerizable hydrophilic polymer interpenetrating the silicone hydrogel polymer matrix. In this example, the non-polymerizable hydrophilic polymer is referred to as an IPN polymer, which acts as an internal wetting agent in the contact lens. In contrast, polymer chains within the silicone hydrogel network that form by polymerization of monomers present in the polymerizable composition are not considered to be IPN polymers. The IPN polymer may be a high molecular weight hydrophilic polymer, for example from about 50,000 to about 500,000 Daltons. In a specific example, the IPN polymer is polyvinylpyrrolidone (PVP). In other examples, the polymerizable composition is substantially free of polyvinyl pyrrolidone or other IPN polymer.

The polymerizable composition may additionally comprise at least one cross-linking agent. As used herein, a "cross-linking agent" is a molecule having at least two polymerizable groups. Thus, a cross-linking agent can react with functional groups on two or more polymer chains so as to bridge one polymer to another. The cross-linking agent may comprise an acryl group or a vinyl group, or both an acryl group and a vinyl group. In certain examples, the cross-linking agent is free of siloxane moieties, i.e., it is a non-siloxane cross-linking agent. A variety of cross-linking agents suitable for use in silicone hydrogel polymerizable compositions are known in the field (see, e.g., U.S. Pat. No. 8,231,218, incorporated herein by reference). Examples of suitable cross-linking agents include, without limitation, lower alkylene glycol di(meth)acrylates such as triethylene glycol dimethacrylate and diethylene glycol dimethacrylate; poly(lower alkylene) glycol di(meth)acrylates; lower alkylene di(meth)acrylates; divinyl ethers such as triethyleneglycol divinyl ether, diethyleneglycol divinyl ether, 1,4-butanediol divinyl ether and 1,4-cyclohexanedimethanol divinyl ether; divinyl sulfone; di- and trivinylbenzene; trimethylolpropane tri(meth)acrylate; pentaerythritol tetra(meth)acrylate; bisphenol A di(meth)acrylate; methylenebis(meth)acrylamide; triallyl phthalate; 1,3-Bis(3-methacryloxypropyl)tetramethyldisiloxane; diallyl phthalate; and combinations thereof.

As will be appreciated by those skilled in the art, the polymerizable composition may comprise additional polymerizable or non-polymerizable ingredients conventionally used in contact lens formulations such as one or more of a polymerization initiator, a UV absorbing agent, a tinting agent, an oxygen scavenger, a chain transfer agent, or the like. In some examples, the polymerizable composition may include an organic diluent in an amount to prevent or minimize phase separation between the hydrophilic and hydrophobic components of the polymerizable composition, so that an optically clear lens is obtained. Diluents commonly used in contact lens formulations include hexanol, ethanol, and/or other alcohols. In other examples, the polymerizable composition is free or substantially free (e.g., less than 500 ppm) of an organic diluent. In such examples, the use of siloxane monomers containing hydrophilic moieties such as polyethylene oxide groups, pendant hydroxyl groups, or other hydrophilic groups, may make it unnecessary to include a diluent in the polymerizable composition. Non-limiting examples of these and additional ingredients that may be included in the polymerizable composition are provided in U.S. Pat. No. 8,231,218.

Non-limiting examples of silicone hydrogels that may be used include comfilcon A, fanfilcon A, stenfilcon A, senofilcon A, senofilcon C. somofilcon A, narafilcon A, delefilcon A, narafilcon A, lotrafilcon A, lotrafilcon B, balafilcon A, samfilcon A, galyfilcon A, and asmofilcon A.

As an option, the silicone hydrogel that forms the contact lens of the present invention is heat-stable prior to any vitamin E being added to the contact lens. Put another way, the vitamin E, when present, in the silicone hydrogel does not alter the heat stability properties of the silicone hydrogel, since the silicone hydrogel was already heat stable. Put another way, the antioxidant contact lens (a) has a heat stability that is no greater than a control contact lens lacking the vitamin E.

Thus, the antioxidant contact lens of the present invention is heat-stable in the absence of any vitamin E. For purposes of the present invention, a contact lens is generally considered heat-stable if the diameter of the fully hydrated contact lens after being autoclaved in a packaging solution is within ±0.2 mm of the diameter of the fully hydrated contact lens before autoclave. As used herein, the diameter of a contact lens refers to the chord diameter. The term "heat-stable" refers to the autoclave-stability of the silicone hydrogel material itself as well as any component that may be embedded within the silicone hydrogel material, such as a drug, releasable polymer or any other beneficial agent. An embedded contact lens component is considered to lack heat-stability if it oxidizes or degrades during autoclaving. In one example, the antioxidant contact lens of the present invention has a heat stability that is no greater than a control contact lens (having no vitamin E present).

In another example, the antioxidant contact lens of the present invention comprises a silicone hydrogel material that is heat-stable in the absence of vitamin E.

In a further example, the antioxidant contact lens of the present invention comprises a silicone hydrogel material that is heat-stable in the absence of vitamin E and does not contain a carotenoid.

As used herein, a "control lens" refers to a contact lens that has no vitamin E present in the lens, but is otherwise identical to the contact lens (i.e. test lens) to which it is being compared in that it was manufactured using the same contact lens formulation (referred to herein sometimes as a "polymerizable composition"), and subjected to the same manufacturing processes. When tested for coefficient of friction (CoF), as described below, the control lens is also subjected to the same overnight wash procedure prior to CoF measurement.

With respect to the antioxidant properties of the contact lens of the present invention, this property can be evidenced by a reduction in peroxidation of lipids in the tear film when the contact lens is worn.

Thus, in the present invention, preferably the antioxidant contact lens contains an amount of vitamin E that reduces peroxidation of lipids in the tear film. One manner in which the reduction can be confirmed and/or quantified is by measuring or studying a model lipid that is present, for instance, linoleic acid or ω-6 essential fatty acid or O-acyl-ω-hydroxyfatty acids, or one or more free fatty acids. In one example, the amount of vitamin E embedded in the contact lens is effective to provide at least a 50%, 60%, 65%, 70%, 75%, 80%, or 85% (in number) reduction in lipid peroxidation relative to a control contact lens lacking the vitamin E when measured in a TBARS assay (thiobarbituric acid reactive substance assay), which is used to test oxidative stress in biological systems by measuring the level of malondialdehyde (MDA), a major lipid oxidation product.

The antioxidant contact lens may contain an amount of vitamin E that reduces the generation of reactive oxygen species (ROS) from human corneal epithelial cells (HCECs) subjected to oxidative stress. One manner in which the reduction of ROS can be confirmed and/or quantified is by comparing the generation of ROS from HCECs contacted with $H_2O_2$ in vitro using an HCEC viability as described in Example 6. In one example, the amount of vitamin E embedded in the contact lens is effective to provide at least a 10%, 25%, 50%, or 75% (in number) reduction in ROS generation relative to a control contact lens lacking the vitamin E when measured in the HCEC viability assay.

As an option, the antioxidant contact lens comprises a silicone hydrogel and at least 10 μg, 15 μg, 20 μg, 25 μg, 50 μg or 100 μg up to about 500 μg, 750 μg or 1000 μg of vitamin E present (e.g. embedded) in the silicone hydrogel.

As an option, the amount of vitamin E present (e.g. embedded) in the silicone hydrogel is at least 10 μg, 15 μg, 20 μg, 25 μg, 50 μg or 100 μg up to about 500 μg, 750 μg or 1000 μg per 25 mg of the silicone hydrogel when fully hydrated (e.g., from 10 μg to 1000 μg per 25 mg of the silicone hydrogel when fully hydrated). Thus, for example, a silicone hydrogel contact lens that contains 50 μg of vitamin E and weighs 20 mg when fully hydrated is considered to contain 62.5 μg vitamin E per 25 mg of the silicone hydrogel.

Because vitamin E is a hydrophobic compound, increasing amounts of vitamin E in a silicone hydrogel contact lens can decrease the surface wettability of the contact lens, particularly in the case of silicone hydrogel contact lenses that lack a post curing surface treatment to impart the lens surface with an ophthalmically-acceptable surface wettability. While decreased surface wettability may be acceptable for a contact lens worn for a limited purpose, such as for the delivery of a drug to treat an infection or ocular disease, decreased wettability is not desirable for a contact lens that is intended to be worn daily to correct the wearer's vision.

Thus, as an aspect of the present invention, the present invention relates to an antioxidant contact lens that reduces peroxidation of lipids yet has an ophthalmically-acceptable surface wettability.

As an option, the antioxidant contact lens has ophthalmically-acceptable surface wettability in the absence of a post-curing surface treatment.

As an option, the surface of the antioxidant contact lens has an advancing contact angle that is no more than 10° greater, or 5° greater than a control lens, where advancing contact angle is measured using the captive bubble method described as described in Example 2.

As indicated, in any options or embodiments of the present invention, the antioxidant contact lens is free of a bioactive agent having a release profile attenuated by the vitamin E (and as indicated, the vitamin E present in the contact lens of the present invention is not considered a bioactive agent.)

Thus, as one aspect, the unworn contact lens has (a) an ophthalmically-acceptable surface wettability in the absence of a post curing surface treatment or (b) an advancing contact angle that is no more than 10° greater than the control lens, or both (a) and (b).

Addition of vitamin E to a silicone hydrogel contact lens material can also decrease the amount of water the lens is capable of absorbing, thereby decreasing the percent equilibrium water content (% EWC) of the contact lens. As used herein the % EWC of a silicone hydrogel contact lens is determined using the method described in Example 2. In certain examples, the % EWC of the antioxidant lens is minimally impacted by the addition of the vitamin E. In a specific example, the antioxidant contact lens has a % EWC that is no less than 10%, or 5% that of a control lens. In some examples, the antioxidant contact lens may have a % EWC of at least 25%, 30%, or 40% up to about 60%, 70%, or 80%. In various examples, the antioxidant contact lens may have a % EWC of about 25 to 45%, 40 to 55% or 50 to 75%. In a specific example, the antioxidant contact lens has a % EWC between 40% to 60%.

Addition of relatively large amounts of vitamin E to a silicone hydrogel contact lens material can result in an increase in lens diameter relative to that of a control lens. In some examples, the diameter of the antioxidant lens is within ±0.5 mm, or ±0.2 mm that of the control lens.

As an option, the unworn contact lens of the present invention is in the absence of any agent that provides antioxidant properties except for the vitamin E.

As an option, in the present invention, the antioxidant contact lens has about the same coefficient of friction after an overnight wash compared to a control lens having no vitamin E in the control lens.

The term "coefficient of friction" refers to the kinetic (dynamic) coefficient of friction (CoF) of a contact lens as measured using a CETR Universal Micro-Tribometer (UMT) or equivalent device. The kinetic (dynamic) coefficient of friction (CoF) of the contact lenses are preferably measured using a CETR Universal Micro-Tribometer (UMT) and CETR UMT Multi-Specimen Testing System software, with a pin-on-disk sample mount at ambient temperature. An adhesive-backed, 2.5" round polyethylene terephthalate film is adhered to the rotational disk, which is mounted on the mounting ring of the UMT. Each contact lens is picked up with tweezers and mounted onto the sample holder. 100 µL PBS is dispensed onto the PET substrate under the lens holder. The center of the lens on the pin tip is pressed against the PBS-wetted PET film moving at a constant sliding speed of 0.5 mm/sec at a constant load of 0.5 g for 12 seconds at a temperature between about 20 degrees C. and 25 degrees C. CoF values are computed by the software, and the average values (n=3) for each lens can be determined.

As used herein, an "overnight wash" is one in which a lens is removed from its packaging solution and soaked in 4 mL PBS for approximately 15 hours at 20° C. to 25° C. (i.e. room temperature).

As an option, in the present invention, the antioxidant contact lens has a coefficient of friction that is the same or about the same (within 15%, or within 10%, or within 5%, or within 1%) as the control lens. As an option, the antioxidant contact lens has a coefficient of friction (after overnight wash) of at least 0.25, at least 0.5, at least 0.75, at least 1.0, at least 1.5, or from about 0.25 to about 1.8, or from about 0.5 to about 1.8, or from about 0.5 to about 1.5.

With the present invention, as an option, there is a balancing of contact lens properties along with the antioxidant properties that are desirable due to the vitamin E being present in the contact lens. The amount of vitamin E can be high to achieve even greater antioxidant properties, however, the inventors of the present invention have determined that if the amount of vitamin E is too high, this can significantly alter the silicone hydrogel properties of the contact lens, such as with respect to surface wettability, advancing contact angle, % EWC, lens diameter, amount of water or aqueous fluid to obtain a fully hydrated contact lens, and the like. Preferably, though not mandatory, the antioxidant contact lens of the present invention has one or more of the same or substantially the same silicone hydrogel properties as a control lens (the same silicone hydrogel contact lens but without any vitamin E present). 'Substantially the same' means within 15%, within 10%, within 5%, or within 1% of one measured property or two or more of the measured properties.

Conventional methods can be used to manufacture the antioxidant contact lens. Typically a polymerizable silicone hydrogel composition is dispensed into a female mold member having a concave surface that defines the front surface of the contact lens. A male mold member having a convex surface that defines the back surface of the contact lens, i.e. the cornea-contacting surface, is combined with the female mold member to form a contact lens mold assembly that is subjected to curing conditions, such as UV or thermal curing conditions, under which the curable composition is formed into a polymeric lens body. The female and male mold members can be non-polar molds or polar molds. The mold assembly is disassembled (i.e. demolded) and the polymeric lens body is removed from the mold and contacted with an organic solvent, such as ethanol, to extract unreacted components from the lens body. The vitamin E may be included in the organic solvent used for the extraction step. After extraction, the lens body is hydrated in an aqueous solution. If vitamin E is included in the extraction solvent, the hydration step will displace the solvent with water, thereby hydrating the contact lens, but the vitamin E will remain embedded within the resulting silicone hydrogel. Exemplary methods of manufacturing silicone hydrogel contact lenses are described in U.S. Pat. No. 8,865,789.

The contact lens in the present invention can be considered a soft contact lens, and particularly a soft silicone hydrogel contact lens. The contact lens sealed in the contact lens package of the present disclosure may be of any lens wear modality. Lens wear modality refers to the how many days and nights in a row the lens can be worn without removal. In one example, the contact lens sealed in the contact lens package of the present disclosure is a daily disposable lens. Daily disposable lenses are indicated for single use, up to about 12 or 16 hours of continuous wear and should be discarded after the single use. In another example, the contact lens sealed in the contact lens package of the present disclosure is a daily wear lens. Daily wear lenses are worn during the waking hours, typically up to about 12 to 16 hours, and are removed before sleep. Daily wear lenses are typically stored in a contact lens case containing a contact lens care solution for cleaning and disinfecting the lens during the hours of non-use. Daily wear lenses are typically discarded after a maximum of 30 days wear. In yet another example, the contact lens is an extended wear lens. Extended wear lenses are typically worn continuously for up to 6, 14 or 30 consecutive days and nights.

The packaging solution sealed within the contact lens package of the present disclosure may be any conventional contact-lens compatible solution. In one example, the packaging solution comprises, consists, or consists essentially, of an aqueous solution of a buffer, and/or a tonicity agent. In another example, the packaging solution contains additional agents such as one or more additional antimicrobial agents, and/or a comfort agent, and/or a hydrophilic polymer, and/or a surfactant and/or other additive that prevents the lens from sticking to the package. The packaging solution can have a pH in the range of about 6.8 or 7.0 up to about 7.8 or 8.0. In one example, the packaging solution comprises phosphate buffer or borate buffer. In another example, the packaging solution comprises a tonicity agent selected from sodium chloride or sorbitol in an amount to maintain osmolality in the range of about 200 to 400 mOsm/kg, and typically from about 270 mOsm/kg up to about 310 mOsm/kg.

With respect to the contact lens package, this package can include or comprise a plastic base member comprising a cavity configured to retain the contact lens and packaging solution and a flange region extending outwardly around the cavity. A removable foil is attached to the flange region to provide a sealed contact lens package. Such contact lens packages, which are commonly referred to as "blister packs", are well-known in the art (see e.g. U.S. Pat. No. 7,426,993). In other examples, the contact lens package comprises a contact lens indicated for daily wear for at least 2 days, wherein the package is configured to allow resealing after its initial opening for subsequent replacement of the lens for overnight storage after it has been worn. For example, the contact lens package may comprise a plastic base member comprising a cavity configured to retain the contact lens and packaging solution and a resealable cover. As used herein, a "resealable cover" is one that is configured to form a liquid-tight or spill-proof seal with the base member after the contact lens package is opened. For example, the plastic base member may comprise a plurality of threads for engagement with a compatible set of threads on a cap which serves as the resealable cover. Such configurations are commonly used in contact lens care cases (see e.g. U.S. Pat. No. 3,977,517). As an option, the contact lens package can serve a dual purpose, i.e. both as a contact lens package for a sterile, unworn contact lens and as a subsequent contact lens carrying case for a worn lens.

It will be appreciated that conventional manufacturing methods can be used to manufacture the sealed contact lens package. Thus, in one aspect of the present disclosure is a method of manufacturing a contact lens package including the step of placing an unworn contact lens and a contact lens packaging solution in a receptacle, placing a cover on the receptacle, and sealing the cover on the receptacle. Generally, the receptacle is configured to receive a single contact lens and an amount of packaging solution sufficient to completely cover the contact lens, typically about 0.5-1.5 ml. The receptacle may be made from any suitable material, such as glass or plastic. In one example, the receptacle comprises a plastic base member comprising a cavity configured to retain the contact lens and packaging solution and a flange region extending outwardly around the cavity, and the cover comprises a removable foil attached to the flange region to provide the sealed contact lens package. The removable foil may be sealed by any conventional means such as heat sealing or gluing. In another example, the receptacle is in the form of a plastic base member comprising a plurality of threads and the cover comprises a plastic cap member comprising a compatible set of thread for engagement with the threads of the base member thereby providing a resealable cover. It will be appreciated that other types of packaging can also be used to provide a resealable package. For example, the contact lens package may comprise a plastic cover comprising features that engage with compatible features of the receptacle to form an interference fit. The method of manufacturing the sealed contact lens package may further comprise sterilizing the unworn contact lens by autoclaving the sealed contact lens package. Autoclaving generally involves subjecting the sealed contact lens package to temperatures of at least 121° C. for at least 20 minutes.

As indicated, the antioxidant contact lens is typically packaged in a packaging solution. A packaging solution may comprise a buffered saline solution such as phosphate- or borate-buffered saline. The packaging solution may optionally contain additional ingredients such as a comfort agent, a hydrophilic polymer, an additive that prevents the lens from sticking to the container, and/or a chelating agent, etc. In some examples, the packaging solution may comprise polysaccharides (e.g. hyaluronic acid, hydroxypropyl methylcellulose, hydroxypropyl cellulose, hydroxyethyl cellulose, etc.) or other high molecular weight polymers, such as polyvinyl pyrrolidone, which are commonly used as comfort polymers or thickening agents in ophthalmic solutions and contact lens packaging solutions.

The antioxidant contact lens is provided unworn (i.e. it is a new contact lens, not having been previously used by a patient), immersed in the packaging solution and sealed in a package. The package may be a blister package, glass vial, or other appropriate container. The package comprises a base member having a cavity for accommodating a packaging solution and an unworn silicone hydrogel contact lens. The sealed package may be sterilized by sterilizing amounts of radiation, including heat or steam, such as by autoclaving, or by gamma radiation, e-beam radiation, ultraviolet radiation, etc.

In a specific example, the packaged antioxidant contact lens is sterilized by autoclaving.

The final product is a sterile, packaged antioxidant silicone hydrogel contact lens having ophthalmically-acceptable surface wettability. In a specific example, the invention provides a contact lens package, comprising a base member having a cavity for accommodating a packaging solution and a contact lens; an unworn silicone hydrogel contact lens in the cavity of the base member; and a packaging solution in the cavity of the base member.

Another aspect of the present invention is directed to a method to control lipid peroxidation from tear film in an eye of a person wearing a contact lens. The method can include the step of inserting a sterile, unworn contact lens in the eye of the person to correct vision in the eye of the person. The sterile, unworn contact lens is a silicone hydrogel contact lens having therein an amount of vitamin E. For instance, at least 10 µg or at least 20 µg of vitamin E per 25 mg of the sterile, unworn contact lens when fully hydrated can be present and 0 µg of a bioactive agent. The other amounts of vitamin E mentioned earlier can be used instead. In the method, the vitamin E is non-releasable from the sterile, unworn contact lens when worn in the eye.

In the method, the method can provide, as an option, at least a 50% reduction in the lipid peroxidation relative to a control contact lens lacking the vitamin E when measured in a TBARS assay. The amount of vitamin E embedded in the contact lens is effective to provide at least a 50%, 60%, 65%, 70%, 75%, 80%, or 85% (in number) reduction in lipid peroxidation relative to a control contact lens lacking the vitamin E when measured in a TBARS assay (thiobarbituric acid reactive substance assay), which is used to test oxidative stress in biological systems by measuring the level of malondialdehyde (MDA), a major lipid oxidation product.

As indicated earlier, in the method, the vitamin E is trapped, embedded, absorbed, or non-covalently attached in the sterile, unworn contact lens, which remains the case once the contact lens is inserted into the eye of the person.

In the method, preferably, the method is conducted in the absence of utilizing any agent that provides antioxidant properties except for the vitamin E.

Any of the embodiments, examples, and options discussed earlier with respect to any of the embodiments for the unworn antioxidant contact lens or seal contact lens package with contact lens can equally be used in the methods of the present invention.

The following Examples illustrate certain aspects and advantages of the present invention, which should be understood not to be limited thereby.

EXAMPLE 1

Silicone hydrogel contact lenses were prepared by curing the formulation for stenfilcon A in polypropylene contact lens molds. The cured stenfilcon A was removed from the molds and extracted by immersing them for 215 minutes in ethanol (EtOH) containing dl-α-tocopherol (DSM Nutritional Products) in the concentrations shown in Table I. The lenses were removed from the EtOH and washed in a mixture of 50/50 EtOH/water for approximately 36 minutes, followed by three exchanges of purified water for approximately 6 minutes, 30 minutes, and 30 minutes, respectively. The lenses were immersed in vials containing PBS and autoclaved.

The vitamin E content of autoclaved lenses that had been extracted in 1.25 mg/mL, 2.5 mg/mL, and 5 mg/mL vitamin E was determined by HPLC analysis. Briefly, each lens (n=5 for each concentration) was removed from its packaging solution, lightly blotted to remove residual packaging, and extracted with 5 ml of methanol at 37° C. for 16 hours. For calibration standards a stock solution of approximately 2000 ppm vitamin E in ethanol was prepared, from which standards of 2, 5, 10 and 25 ppm in methanol were made. A C18 Symmetry 4.6×150 mm column was used at 45° C. with 50 µL injection volumes. The detection wavelength was 293 nm. The lens extracts were diluted with methanol before injection. The average amount of vitamin E loaded in the lenses is shown in Table 1. To determine whether vitamin E leaches from the lenses during autoclave, the packaging solutions were diluted 50:50 (by volume) in methanol and tested by HPLC. Vitamin E was not detected in any of the packaging solutions (LOD is ~0.1 ppm), indicating that the vitamin E does not elute from the lens. Lenses extracted with 2.5 mg/mL vitamin E were stored at 45° C. for 1 month and the lens and packaging solution were tested for vitamin E content by HPLC. The lenses (n=5) contained an average of 207 µg vitamin E and vitamin E was not detected in any of the packaging solutions, indicating that the vitamin E-containing lenses have good shelf stability.

EXAMPLE 2

The average (n=5) diameter, % equilibrium water content, and advancing contact angle of lenses made according to Example 1 were measured using the methods described below. Results are shown in Table 1.

Diameter. An Optimec model JCF contact lens dimension analyzer was used to measure the diameter of fully hydrated lenses.

% EWC. To measure percent equilibrium water content (% EWC) the weight of a hydrated lens with excess surface water wiped off is measured. The lens is fully dried in an 80° C. oven under vacuum and weighted to obtain the dry weight and the difference between the hydrated weight and the dry weight is calculated. The % EWC of the lens=(weight difference/hydrated weight)×100.

Contact angle. The surface wettability of the lenses was determined by measuring averages advancing contact angle using a captive bubble method and a drop shape analyser (DSA 100, Krüss GmbH, Hamburg, Germany) at room temperature as described in Maldonado-Codina, C. and Morgan, P. B. (2007), J. Biomed. Mat. Res. 83A:496-502. The contact angle values provided in Table 1 are the average of measurements from five lenses.

EXAMPLE 3

The TBARS assay protocol described below was adapted from D. Impellizzeri et al. (2015) Eur J Pharmacol, 761:28-35.

Sample preparation. Lens from Example 1 were removed from the packaging solution and lightly blotted to remove carry-over packaging solution. A 6 mm diameter circle was punched out of each lens and placed on a petri dish. 5 µl of a 20% solution of linoleic acid (LA) in isopropyl alcohol (IPA) was applied to the surface of each punch out. Each punch-out was dried for 15 minutes at room temperature and placed into an amber HPLC vial. To subject the LA to oxidization conditions the vials were placed in a 37° C. incubator with a plexiglass cover and exposed to air at ambient light for 72 hours. To extract LA and LA oxidation products from the punch-outs, 1 mL IPA was added to each vial and the vials were placed on a shaker at room temperate for about 45 minutes.

TBAR reagent preparation. The following reagents are prepared in dH$_2$O: 1.15% KCl, 8.1% lauryl sulfate (LS), 20% acetic acid (AA), and 0.8% thiobarbituric acid (TBA). Each 4.0 mL of TBARS reaction mixture consists of 100 µl KCl, 200 µl LS, 1.5 mL AA, 1.5 mL TBA, 700 µl dH$_2$O. The calibration standard, malondialdehyde modified bovine serum albumin (MDA-BSA) (Cell Biolabs, Inc., Cat. #STA-832) was diluted to 1 mg/mL in dH$_2$O.

TBAR Assay Procedure.

25 µl of extract from each punch-out is added to a test tube containing 475 µl of the TBARS reaction mixture. The tubes are placed in a boiling water bath for 60 minutes then removed from the water bath and allowed to cool to room temperature. Each tube is centrifuged for 10 minutes at 3000×g (RCF). 200 µl from each tube is transferred to the well of a 96-well plate and absorbance @ 520 nm is measured. For the standard curve, 10 µl of the MDA-BSA (1 mg/ml) was added to 0.99 mL of the TBARS reaction mixture to provide 1.0 mL of a 10 µg/mL MDA-BSA standard. Successive serial dilutions were made into TBARS mixture to provide standards of 5 µg/mL, 2.5 µg/mL, 1.25 µg/mL, 0.625 µg/mL, 0.313 µg/mL, and 0.156 µg/mL and absorbance @ 520 nm was measured.

The average amount of MDA present in the extract from each lens punch-out was determined using the standard curve. The % oxidation inhibition provided by the vitamin E-containing lenses was determined by the formula: 100* [(µg MDC$_{control}$−µg MDC$_{sample}$)/µg MDC$_{control}$].

TABLE 1

| Vit. E Conc. In EtOH | Amt. Vit E in Lens | Diameter (mm) | % EWC | Advancing Contact Angle | % Oxidation Inhibition |
|---|---|---|---|---|---|
| 0 mg/ml (Control) | 0 | 14.2 | 54.7 | 50.0 | 0 |
| 0.1 mg/mL | n/a | 14.2 | 54.3 | 49.8 | 0 |
| 0.3 mg/mL | n/a | 14.3 | 54.6 | 51.2 | 81 |
| 0.6 mg/mL | n/a | 14.1 | 54.6 | 50.6 | 80 |
| 1.25 mg/mL | 103 µg | 14.1 | 54.3 | 52.0 | 85 |
| 2.5 mg/mL | 204 µg | 14.2 | 54.0 | 50.7 | 83 |
| 5 mg/mL | 500 µg | 14.3 | 53.1 | 51.8 | 81 |
| 10 mg/mL | n/a | 14.2 | 51.4 | 53.0 | 79 |
| 20 mg/mL | n/a | 14.2 | 48.4 | 53.4 | 83 |
| 40 mg/mL | n/a | 14.4 | 43.4 | 58.4 | 87 |

EXAMPLE 4

Polymerized comfilcon A was removed from the lens molds and extracted in ethanol containing the concentrations of vitamin E shown in Table 2. The lenses were hydrated, autoclaved, and tested for antioxidant properties using the TBARS assay described in Example 3. The results are provided in Table 2.

TABLE 2

| Vit. E Conc. In EtOH | % Oxidation Inhibition |
|---|---|
| 0 mg/ml (Control) | 0 |
| 0.1 mg/mL | 67 |
| 0.3 mg/mL | 82 |
| 0.6 mg/mL | 84 |
| 1.25 mg/mL | 87 |
| 2.5 mg/mL | 84 |
| 5.0 mg/mL | 88 |

EXAMPLE 5

Vitamin E was loaded into stenfilcon A and comfilcon A lenses as described above. Vitamin E loading and EWC were measured. Results are provided in Table 3.

TABLE 3

| Lens Material | Vit. E Conc. In EtOH | Amt. Vit E in Lens (μg) | Dry lens weight (mg) | Wet lens weight (mg) | EWC (%) |
|---|---|---|---|---|---|
| Comfilcon A | 0 | 0 | 15.4 | 29.4 | 47.4 |
| Comfilcon A | 0.3 mg/mL | 23 | 14.2 | 26.8 | 47.1 |
| Comfilcon A | 2.5 mg/mL | 221 | 14.8 | 27.67 | 46.3 |
| Stenfilcon A | 0 mg/mL | 0 | 14.2 | 31.4 | 54.7 |
| Stenfilcon A | 5 mg/mL | 509 | 16.0 | 33.3 | 52.0 |

EXAMPLE 6

HCEC Viability Assay. Immortalized cultured human corneal epithelial cells (HCEC) (e.g. 2.040 pRSV-T (ATCC® CRL-11516™)) are seeded into wells of a 24-well cell culture plate and allowed to adhere and grow to confluence using a suitable growth media such as a supplemented hormonal epithelial medium (SHEM) described by Loureiro et al. (Mol Vis 2013; 19:69-77). $H_2O_2$ is diluted with unbuffered 0.9% saline to provide $H_2O_2$ solutions ranging from 0.03% to 3%. Growth media is removed from the wells and a volume 1 mL of each $H_2O_2$ solution sufficient to cover the confluent HCECs is applied to each well (n=4) for 1 hour. Cell viability is determined using alamarBlue™ HS Cell Viability Reagent and protocol (ThermoFisher Scientific Cat. #A50100). An $H_2O_2$ concentration that reduces HCEC viability to an average of about 70% is selected for further testing.

HCEC cells are grown to confluence in cell culture wells as described above. Growth media is removed from the wells and an antioxidant or control lens is placed in each well (n=4) so that the anterior surface of the lens comes into contact with the cell layer. 1.5 mL of serum-free maintenance medium (e.g. DMEM containing insulin, transferrin, and sodium selenite (DMEM-ITS) described by Suzuki et al. (J. Curr Eye Res 2000; 20:2, 127-130) is placed in each well and the cells are incubated overnight. The media is removed from the cells leaving the lens in the wells, and 1 mL of the $H_2O_2$ solution at the concentration identified above is applied to each well. After 2 hours the amount of reactive oxygen species (ROS) in the $H_2O_2$ solution is quantified by the TBARS/MDA assay previously described in Example 3.

The disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

The entire contents of all cited references in this disclosure, to the extent that they are not inconsistent with the present disclosure, are incorporated herein by reference.

The present invention can include any combination of the various features or embodiments described above and/or in the claims below as set forth in sentences and/or paragraphs. Any combination of disclosed features herein is considered part of the present invention and no limitation is intended with respect to combinable features.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An unworn antioxidant contact lens immersed in a packaging solution and sterilely sealed in a package, said contact lens comprising a silicone hydrogel and amount of vitamin E embedded within the silicone hydrogel effective to provide at least a 50% reduction in lipid peroxidation relative to a control contact lens lacking the vitamin E when measured in a TBARS assay, wherein the antioxidant contact lens is free of a bioactive agent having a release profile attenuated by the vitamin E.

2. An unworn antioxidant contact lens immersed in a packaging solution and sterilely sealed in a package, said contact lens comprising a silicone hydrogel and amount of vitamin E embedded within the silicone hydrogel effective to provide at least a 50% reduction in lipid peroxidation relative to a control contact lens lacking the vitamin E when measured in a TBARS assay, wherein the antioxidant contact lens has (a) an ophthalmically-acceptable surface wettability in the absence of a post curing surface treatment and (b) an advancing contact angle that is no more than 10° greater than the control lens.

3. An unworn antioxidant contact lens immersed in a packaging solution and sterilely sealed in a package, said contact lens comprising a silicone hydrogel and 10 μg to 1000 μg of vitamin E embedded in the silicone hydrogel, wherein the antioxidant contact lens (a) has a heat stability that is no greater than a control contact lens lacking the vitamin E and (b) is free of a bioactive agent having a release profile attenuated by the vitamin E.

4. The unworn antioxidant contact lens of claim 1, wherein the amount of vitamin E is 10 μg to 1000 μg per 25 mg of the antioxidant contact lens when fully hydrated.

5. The unworn antioxidant contact lens of claim 1 having a % equilibrium water content (% EWC) that is no less than 5% that of the control lens.

6. The unworn antioxidant contact lens of claim 1 having between 40% to 60% EWC.

7. The unworn antioxidant contact lens of claim 1 having a lens diameter within ±0.2 mm that of the control lens.

8. The unworn antioxidant contact lens of claim 1 having an advancing contact angle that is no more than 5° greater than the control lens.

9. The unworn antioxidant contact lens of claim 1 wherein the reduction in lipid peroxidation is at least 80%.

10. The unworn antioxidant contact lens of claim 1, wherein the amount of vitamin E is effective to reduce generation of reactive oxygen species (ROS) from human corneal epithelial cells (HCECs) contacted in vitro with $H_2O_2$ relative to the control contact lens when measured in an HCEC viability assay.

* * * * *